United States Patent [19]

Fujino et al.

[11] 4,337,247
[45] Jun. 29, 1982

[54] TETRAPEPTIDESEMICARBAZIDE DERIVATIVES AND THEIR PRODUCTION AND USE

[75] Inventors: Masahiko Fujino, Takarazuka; Mitsuhiro Wakimasu, Suita; Kiyohisa Kawai, Nagaokakyo, all of Japan

[73] Assignee: Takeda Chemical Industries, Ltd., Osaka, Japan

[21] Appl. No.: 213,683

[22] Filed: Dec. 5, 1980

[30] Foreign Application Priority Data

Dec. 27, 1979 [JP] Japan ................................. 54-173608

[51] Int. Cl.³ ...................... A61K 37/00; C07C 103/52
[52] U.S. Cl. .............................. 424/177; 260/112.5 E
[58] Field of Search .................. 260/112.5 E; 424/177

[56] References Cited

U.S. PATENT DOCUMENTS 4,178,371 12/1979 Morgan ........................ 260/112.5 E Primary Examiner—Delbert R. Phillips
Attorney, Agent, or Firm—Wegner & Bretschneider

[57] ABSTRACT

Novel tetrapeptidesemicarbazide derivatives, inclusive of a pharmacologically acceptable salt thereof, which has the general formula (I):

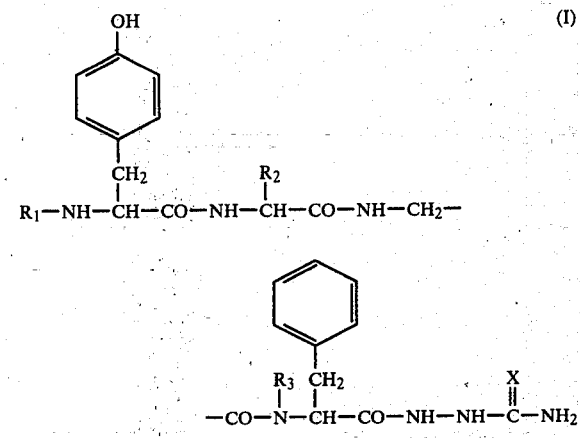

wherein $R_1$ is hydrogen or lower alkyl; $R_2$ is hydrogen or a D-α-amino acid side chain; $R_3$ is hydrogen or lower alkyl; X is oxygen or sulfur, are useful as analgesics.

25 Claims, No Drawings

TETRAPEPTIDESEMICARBAZIDE DERIVATIVES AND THEIR PRODUCTION AND USE

This invention relates to new tetrapeptidesemicarbazide derivatives having analgesic actions.

Hughes et al [Nature 258, 577 (1975)] isolated from the pig brain a pair of pentapeptides displaying morphinomimetic activity on intracerebral administration, i.e. enkephalins, and determined their chemical structures, i.e. H-Tyr-Gly-Gly-Phe-Met-OH and H-Tyr-Gly-Gly-Phe-Leu-OH. While these substances show morphinomimetic activity on direct intracerebral administration, they do not produce analgesic effects when administered by the intravenous route. On the other hand, β-endorphine which is considered to be derived from the carboxy-terminal of β-lipotrophine displays an overt analgesic action even if administered intravenously, but being a polypeptide consisting of 31 amino acids, it can be produced by organic chemistry procedures only with considerable difficulty and, therefore, cannot be made available in a sufficient quantity for pharmaceutical use.

The present inventors investigated the possibility of securing a compound which would be economically advantageous, stable as a chemical compound and able to provide a sufficient analgesic effect on administration by the intravenous or subcutaneous route. The investigation led to the discovery that certain tetrapeptidesemicarbazide derivatives are suited for the above-mentioned purpose. The above finding was followed by further research which has eventually resulted in the present invention.

This invention is, therefore, directed to:

(1) a tetrapeptidesemicarbazide derivative of general formula (I) or a pharmacologically acceptable salt thereof:

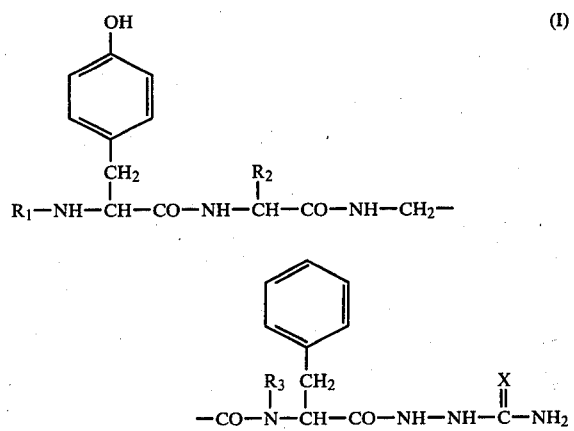

(I)

wherein $R_1$ is hydrogen or lower alkyl; $R_2$ is hydrogen or a D-α-amino acid side chain; $R_3$ is hydrogen or lower alkyl; X is oxygen or sulfur.

(2) a method of producing a tetrapeptidesemicarbazide derivative of general formula (I):

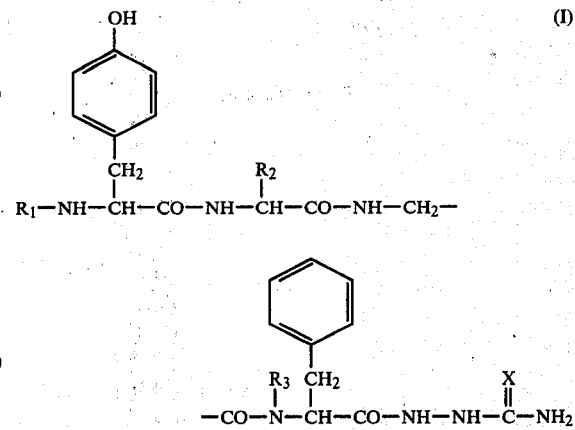

(I)

wherein $R_1$ is hydrogen or lower alkyl; $R^2$ is hydrogen or a D-α-amino acid side chain; $R_3$ is hydrogen or lower alkyl; X is oxygen or sulfur, which is characterized by deprotecting a compound of general formula (II):

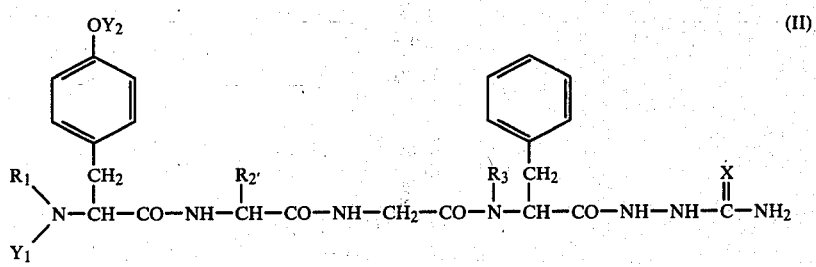

(II)

wherein $R_1$, $R_3$ and X are as defined above; $R_{2'}$ is hydrogen or a D-α-amino acid side chain which may optionally be substituted; $Y_1$ is a protective group; $Y_2$ is hydrogen or a protective group; and (3) an analgesic containing a tetrapeptidesemicarbazide derivative of general formula (I) or a pharmacologically acceptable salt thereof.

In this specification, amino acids and peptides are designated either by the abbreviations commonly used in the art or by those adopted by the Committee on Chemical Nomenclature of IUPAC-IUB. Some of such abbreviations are as follows.

Ala: alanine
Gly: glycine
Leu: leucine
Phe: phenylalanine
Asp: aspartic acid
Asn: asparagine
Glu: glutamic acid
Gln: glutamine
MePhe: N-methyl-phenylalanine
EtPhe: N-ethyl-phenylalanine
Tyr: tyrosine
Met(O): methioninesulfoxide
MeTyr: N-methyl-tyrosine In the following description, the compounds repeatedly referred to are designated by the following abbreviations.

DCC: N,N'-dicyclohexylcarbodiimide
HONB: N-hydroxy-5-norbornene-2,3-dicarboximide
ONB: HONB ester
Tos: tosyl
Z: benzyloxycarbonyl
BOC: t-butoxycarbonyl
Bu$^t$: t-butyl
DMF: dimethylformamide
Bzl: benzyl
HOBT: N-hydroxybenzotriazole
MeOH: methyl alcohol
AcOEt: ethyl acetate
TEA: triethylamine
DCHA: dicyclohexylamine
DCU: N,N'-dicyclohexylurea
OSu: N-hydroxysuccinimide ester
OMe: methyl ester
OEt: ethyl ester
THF: tetrahydrofuran
TFA: trifluoroacetic acid Throughout this specification, wherever any amino acid or its residue is designated by an abbreviation in the above manner, it represents the L-form thereof unless otherwise specified, while the D-form of any amino acid or residue thereof is specified by (D)- or D-.

Referring, now, to the above general formulas, the lower alkyl $R_1$ is preferably an alkyl group of 1 to 3 carbon atoms, such as methyl, ethyl, n-propyl and isopropyl.

The side chain of D-α-amino acid as represented by $R_2$ or $R_2'$ is the side chain of any of such amino acids as D-leucine, D-alanine, D-methionine, D-methioninesulfoxide, D-methioninesulfone, D-serine, D-threonine, D-phenylalanine, D-α-aminobutyric acid, D-valine, D-norvaline, D-norleucine, D-isoleucine, D-histidine, D-tryptophan, D-tyrosine, D-glutamine, D-asparagine, D-arginine, D-lysine, D-ornithine, D-glutamic acid, D-aspartic acid, D-cysteine, S-methyl-D-cysteine, S-ethyl-D-cysteine, S-methyl-D-cysteinesulfoxide, S-ethyl-D-cysteinesulfoxide, S-methyl-D-methionine, O-t-butyl-D-serine, O-t-butyl-D-threonine, D-aspartic acid-β-methyl ester and D-glutamic acid-γ-methyl ester. Particularly desirable is methionine sulfoxide.

Lower alkyl $R_3$ may for example be any of alkyls mentioned for $R_1$.

As examples of the protective group $Y_1$ in the above general formula, there may be mentioned benzyloxycarbonyl, t-butoxycarbonyl, t-amyloxycarbonyl, isobornyloxycarbonyl, adamantyloxycarbonyl, chloro- or nitro-substituted benzyloxycarbonyl, o-phenylthio and diphenylphosphinomethyl. The protective group $Y_2$ may for example be benzyl and t-butyl.

As regards the protective group on $R_{2'}$, the protective group for protecting the hydroxy group of each parent group may for example be one of the groups mentioned for $Y_2$.

A peptide derivative of chemical structural formula (I) is produced by condensing an amino acid or peptide fragment capable of forming polypeptide (I) with the remaining part of the polypeptide. Thus, for example, the following alternative methods may be utilized for this purpose. The methods described in M. Bodansky and M. A. Ondetti: Peptide Synthesis, Interscience, New York, 1966 F. M. Finn and K. Hofman: The Proteins, Vol. 2, ed. by H. Nenrath, R. L. Hill, Academic Press Inc., New York, 1976; or Nobuo Izumiya et al; Peptide Gosei (Peptide Synthesis), Maruzen Inc., 1975, may be utilized. Thus, for example, the azide method, chloride method, acid anhydride method, mixed acid anhydride method, DCC method, active ester method, the method involving the use of Woodward's reagent K, carbodiimidazole method, reduction-oxidation method and DCC/HONB method may be mentioned. There are cases in which the NCA (N-carboxy-anhydride) method (the method involving the use of an intramolecular cyclic carbonyl compound corresponding to the amino acid without use of a protective group) may be utilized.

Prior to the condensation reaction, the carboxyl or/and amino group in starting material which will not be pertinent to the reaction may be previously protected or the carboxyl or/and amino groups of starting material which are pertinent to the reaction may be previously activated.

Usually, various protected phenylalanine semicarbazide derivatives which are produced by coupling N-protected phenylalanine with semicarbazide or thiosemicarbazide may be used for producing tetrapeptidesemicarbazide derivatives of the general formula (I).

The protective groups for the starting material may be the protective groups mentioned hereinbefore. The carboxyl group of the starting material may also be protected in the form of metal salt (e.g. sodium salt, potassium salt), t-alkylamine salt (e.g. triethylamine salt, N-methylmorpholine salt) or ester (e.g. methyl ester, ethyl ester, benzyl ester, p-nitrobenzyl ester, t-butyl ester, t-amyl ester). As examples of the protective group for the amino group in the starting material, there may be mentioned benzyloxycarbonyl, t-butoxycarbonyl and isobornyloxycarbonyl. The imino group of histidine may be protected by benzyl, tosyl, 2,4-dinitrophenyl, t-butyloxycarbonyl and carbobenzoxy. The hydroxyl group of tyrosine may be protected in the ether form by benzyl and t-butyl.

As examples of the activated form of the carboxyl group in the starting material, there may be mentioned the corresponding acid anhydride, azide, active ester [i.e. esters with alcohols (e.g. pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide, N-hydroxybenzotriazole)]. As an example of the activated form of the amino group in the starting material, there may be mentioned the corresponding phosphoric acid amide.

Assuming that the starting materials are A and B, the above combinations of carboxyl and amino groups in starting materials may be as shown in the following Table 1.

TABLE 1

| Combination Example | Starting materials | | | |
|---|---|---|---|---|
| | A | | B | |
| | COOH | NH$_2$ | COOH | NH$_2$ |
| 1* | Free | Protected | Protected | Free |
| 2 | Activated | Protected | Free | Free |
| 3 | Free | Protected | Protected | Activated |

Note:
In the case of *, a dehydrating agent (e.g. a carbodiimide reagent such as dicyclohexylcarbodiimide) is desirably present in the reaction system.

The reaction may be carried out in a solvent. This solvent is selected from among the solvents hitherto-known to be suited for peptide synthesis reactions. Thus, for example, there may be mentioned anhydrous or aqueous dimethylformamide, dimethylsulfoxide, pyridine, chloroform, dioxane, dichloromethane and tetrahydrofuran as well as appropriate mixtures of such solvents.

The reaction temperature is selected from the range hitherto-known to be suited for peptide synthesis reactions and may normally range from about −20° C. to 30° C. The precursor compounds (protected peptides) for the compounds of this invention may be easily produced as well by the solidphase synthesis procedure.

The protected compound of formula (II) so obtained is subjected to a deprotecting reaction by which the protective groups are removed. While the deprotecting reaction depends on the type of protective group involved, it is preferred for commercial purposes that this reaction is such that it removes all the protective groups in a single step without affecting the peptide bonds. Thus, protective groups are chosen in consideration of this possibility. Table 2 shows some combinations of different types of protective groups and typical deprotecting conditions.

TABLE 2

| Conditions of removal | Protective group $Y_1$ | $Y_2$ | Protective group on $R_{2'}$ |
|---|---|---|---|
| H$_2$/catalyst | Z | Bzl | — |
| H$_2$/catalyst | Z | — | — |
| CF$_3$COOH | BOC | Bu$^t$ | Bu$^t$ |
| 2N-HCl | BOC | — | — |
| (in acetic acid) | BOC | — | — |
| CH$_3$SO$_3$H | Z | — | — |

While Table 2 is a listing of some deprotecting reactions such as catalytic reduction involving the use of palladium black, palladium-on-carbon, platinum or the like catalyst and acid hydrolysis with trifluoroacetic acid, dilute hydrochloric acid or methanesulfonic acid, such other processes as reduction with sodium metal in liquid ammonia and acid hydrolysis with the use of trifluoromethanesulfonic acid, a solution of hydrogen bromide in glacial acetic acid, hydrogen fluoride or the like may also be mentioned. These reactions are generally conducted at suitable temperatures from −20° C. to 40° C., and in the case of acid hydrolysis, the addition of a cation acceptor such as anisole, phenol or thioanisole is advantageous.

After completion of the reaction, the tetrapeptidesemicarbazide derivative (I) so produced is isolated by procedures which are known for the separation of peptide derivatives, i.e. by extraction, distribution, reprecipitation, recrystallization or column chromatography.

The compound (I) may be obtained in the form of a salt, e.g. the organic acid salt or inorganic acid salt, preferably acetate, citrate, tartrate, hydrochloride or sulfate.

When $R_2$ is the side chain of D-glutamic acid or D-aspartic acid and its ω-carboxyl group is a free radical, the compound (I) can be secured as an alkali salt. The alkali salt may for example be the sodium or potassium salt.

The following is the result of a pharmacological test with the compound (I) of this invention.

Hot-plate test

Ta:CF$_1$ mice, 4 weeks old and with body weights 18–22 g, were used. When the animal is placed on a hot copper plate maintained at 55°±0.5° C., it shows certain responses to the thermal stimulus such as licking the soles of the hind paws or jumping up to escape. The mice showing such responses within 20 seconds after placement on the hot plate were selected into groups of 10 animals. The test drug was injected intravenously or subcutaneously, and after 5, 10, 20, 30, 45 and 60 minutes, their response times were measured and compared with the response times of untreated animals (control groups). To avoid irreversible injuries to the soles, 60 seconds was selected as the maximum test time. The indexes of analgesic action (response prolongation rate, %) were derived by means of the following equation and a Student's t-test was carried out to evaluate the effectiveness of the test drug.

$$\text{Analgesic activity (\%)} = \frac{\text{Response time after dosing (sec.)} - \text{Response time before dosing (sec.)}}{60 - \text{response time before dosing (sec.)}} \times 100$$

In the above test, the compound (I) of this invention in doses of no more than 1 mg/kg displayed analgesic actions equivalent to a prolongation rate of not less than 40% with a peak occurring at 5 to 60 minutes and some particularly effective species of compound (I) displayed marked pain reliefs even in small doses not exceeding 0.1 mg/kg.

As mentioned hereinbefore, the compound (I) according to this invention produces a definite analgesic action, as evidenced by results of hot-plate tests in mice, at the subcutaneous dose levels between about 0.05 to 10 mg/kg, and in view of its superior efficacy as compound with β-endorphine, is of value as an analgesic drug. The compound (I) is also expected to have neurotropic activity.

Compared with the conventional enkephalin homologs, the compound (I) is characterized by a remarkably low sodium ratio. Thus, in measurements with the morphine receptors separated from the mouse brain, the binding force ratio in the presence of sodium versus the absence of sodium is regarded as an important pharmacologic factor but the compound of this invention shows a very low sodium ratio. This fact indicates that the compound is different from the known enkephalin homologs in pharmacological properties.

The compound (I) of this invention further has a strong gastrointestinal motility inhibitory activity and is, therefore, useful as a drug for the treatment of gastrointestinal disturbances such as diarrhea.

Therefore, the compound (I) and its pharmacologically acceptable salts can for instance be used as analgesics for the relief of pains inclusive of the pain of advanced-stage cancer and as medicaments for the treatment of gastrointestinal disorders such as diarrhea, in mammalian animals such as mouse, rat, rabbit, dog, monkey and human being etc. or be used as medicaments for the treatment of mental diseases such as schizophrenia.

The compound (I) and its pharmacologically acceptable salts, which are provided by this invention, are extremely low in toxicity and no death is encountered even at the dose level of 200 mg/kg which is by far beyond the effective dose.

The compound of this invention may be administered in its free form or as a suitable salt thereof. In the case of free compound (I), the proper dosage is generally in the range of 0.01 to 20 mg/kg. The dosage of the salt of (I) may also range generally from 0.01 to 20 mg/kg, as free compound (I). The compound and its salts according to this invention are mainly administered by routes other than the oral route (e.g. intravenous, subcutaneous, rectal), although they may be orally applied depending on condition. Particularly useful is continuous infusion or instillation in the course of a surgical operation.

Useful dosage forms include injections, suppositories, powders and so forth, although instillable preparations are also useful. Particularly desirable are injectable preparations. Being stable substances, the compounds according to this invention can be stored as dissolved in physiological saline. In the case of intravenous and subcutaneous injections, concentrations of the compound (I) are preferably within the range of 1 to 20 mg/ml in physiological saline.

Injectable preparations can be produced, for example, in the following manner. Thus, 5 mg of compound (I) is dissolved in 2 ml of physiological saline, dispensed into ampoules and, after sealing, the ampoules are heat-sterilized at 110° C. for 30 minutes. Alternatively, 1 to 3 mg of compound (I) and 20 mg of mannitol or sorbitol are dissolved in 2 ml of distilled water, the solution is dispensed into ampoules, lyophilized and sealed. To use the lyophilized compound (I), the ampoule is unsealed and dissolved in physiological saline at the concentration of 1 to 20 mg/ml. This solution can be administered intravenously or intramuscularly.

Like compound (I), several species of the compound (II) also have analgesic activity.

The following examples are given to describe this invention in further detail. It should be understood that the Sephadex LH-20 used for the purification of final products is the product of Pharmacia (Sweden) and that the purity of each compound prepared was assayed by thin-layer chromatography on Kieselgel 60F-254, Merck (West Germany) using the following solvent systems:

Rf$^1$: chloroform-methanol-acetic acid (9:1:0.5)

Rf$^2$: ethyl acetate-pyridine-acetic acid-water (60:20:6:10)

EXAMPLE 1

Production of H-Tyr-(D)-Met(O)-Gly-MePhe-NHNHCONH$_2$ (I) Production of Z-MePhe-NHNHCONH$_2$ In 5 ml of water is dissolved 2.50 g (22 mM) of NH$_2$NHCONH$_2$.HCl, the solution is neutralized with 3.14 ml of TEA, and 40 ml of DMF is added. In this solution are dissolved 6.26 g (20 mM) of Z-MePhe-OH and 4.01 g of HONB, and after ice-cooling, 4.90 g of DCC is added. The mixture is stirred for 24 hours, the precipitated DCU filtered off, the solvent distilled off and the residue dissolved in 200 ml of ethyl acetate. The solution is washed with 4% aqueous sodium hydrogen carbonate and 1 N-aqueous HCl and dried over anhydrous sodium sulfate. The solvent is distilled off and the residue dissolved in chloroform and chromatographed on a silica gel column (5.5×13 cm), elution being carried out with 5% MeOH/CHCl$_3$. The fractions from 600 ml to 2 l are pooled, concentrated and treated with ether-petroleum benzine to obtain a powder. Yield 6.10 g (82.3%); m.p. 69°–72° C.; $[\alpha]_D^{24} -42.5°$ (c=0.94, DMF); Rf$^1$ 0.45.

Elemental analysis, for C$_{19}$H$_{22}$O$_4$N$_4$: Calcd. C, 61.61; H, 5.99; N, 15.13. Found C, 61.58; H, 6.15; N, 14.53.

(II) Production of BOC-(D)-Met-Gly-OEt

In 100 ml of THF are dissolved 10.0 g of BOC-(D)-Met-OH and 7.9 g of HONB, and after cooling to 0° C., 9.0 g of DCC is added. The mixture is stirred at 0° C. for 6 hours. The insolubles are filtered off, 5.9 g of H-Gly-OEt.hydrochloride and 5.6 ml of TEA are added to the filtrate and the mixture is stirred at room temperature overnight. The THF is distilled off and the residue is extracted with 100 ml of AcOEt, washed with water and dried over anhydrous sodium sulfate. The AcOEt is distilled off and the residue is crystallized from petroleum benzine and further recrystallized from AcOEt-petroleum benzine. Yield 9.8 g; m.p. 55°–56° C.; Rf$^1$=0.70; $[\alpha]_D^{21} +12.5°$ (c=0.67, DMF).

Elemental analysis, for C$_{14}$H$_{26}$O$_5$N$_2$S: Calcd. C, 50.28; H, 7.83; N, 8.37; S, 9.59. Found C, 50.88; H, 7.99; N, 8.46; S, 9.42.

(III) Production of BOC-Tyr-(D)-Met-Gly-OEt

In 15 ml of TFA is dissolved 3.0 g of BOC-(D)-Met-Gly-OEt and the solution is allowed to stand at room temperature for 10 minutes. The TFA is distilled off and the residue is treated with diethyl ether and filtered. The resulting powder is dissolved in 20 ml of THF, and after cooling, 1.6 ml of TEA and 4.0 g of BOC-Tyr-ONB are added. The mixture is stirred at room temperature overnight. The THF is distilled off and the residue is extracted with 100 ml of AcOEt, washed with water and dried over anhydrous sodium sulfate. The AcOEt is distilled off and the residue is crystallized from petroleum benzin and recrystallized from AcOEt. Yield 3.1 g; m.p. 121°–122° C.; Rf$^1$=0.62; $[\alpha]_D^{21} +16.8°$ (c=0.40, DMF).

Elemental analysis, for C$_{23}$H$_{35}$O$_7$N$_3$S: Calcd. C, 55.51; H, 7.09; N, 8.44; S, 6.44. Found C, 55.32; H, 6.93; N, 8.25; S, 6.27.

(IV) Production of BOC-Tyr-(D)-Met-Gly-OH

In 30 ml of MeOH is dissolved 2.8 g of BOC-Tyr-(D)-Met-Gly-OEt, after cooling 12 ml of 1 N-aqueous sodium hydroxide is added and the mixture is stirred at room temperature for 1 hour. After cooling, 60 ml of 0.2 N-aqueous HCl is added and resulting crystals are recovered by filtration and washed with cold water. Yield 2.3 g; m.p. 184°–186° C.; Rf$^1$=0.24; $[\alpha]_D^{21} +13.3°$ (c=0.46; DMF).

Elemental analysis, for C$_{21}$H$_{31}$O$_7$N$_3$S: Calcd. C, 53.71; H, 6.65; N, 8.94; S, 6.83. Found C, 54.32, H, 6.71; N, 8.49; S, 6.70.

(V) Production of BOC-Tyr-(D)-Met-Gly-MePheNHNHCONH$_2$

In 20 ml of methanol is dissolved 0.87 g of Z-MePhe-NHNHCONH$_2$ and catalytic reduction is carried out in the presence of palladium black catalyst for 5 hours. The catalyst is filtered off, the filtrate is concentrated and the residue is dissolved in 15 ml of DMF. To this solution are added 1.0 g of BOC-Tyr-(D)-Met-Gly-OH and 0.42 g of HONB, and after cooling with ice, 0.49 g of DCC is added and stirred for 24 hours. The precipitated DCU is filtered off, the solvent is distilled off and the residue is dissolved in n-butanol-containing ethyl acetate, washed with aqueous sodium hydrogen carbonate and aqueous acetic acid and dried over anhydrous sodium sulfate. The solvent is distilled off, and the residue dissolved in chloroform and subjected to silica gel column (3.8×4 cm) chromatography, elution being carried out with chloroform-methanol-acetic acid (25:2:1). The fractions from 70 to 180 ml are pooled, concentrated, treated with ether and petroleum benzine and filtered to obtain a powder. Yield 0.45 g (31%); m.p. 130°–134° C.; $[\alpha]_D^{24} -28.9°$ (c=1.10, DMF); $Rf^1$ 0.21.

Elemental analysis, for $C_{32}H_{45}O_8N_7S.3/2H_2O$: Calcd. C, 53.76; H, 6.77; N, 13.72; S, 4.49. Found C, 53.80; H, 6.35; N, 13.56; S, 4.52.

(VI) Production of BOC-Tyr-(D)-Met(O)-Gly-MePhe-NHNHCONH$_2$

In 3 ml of acetic acid is dissolved 0.35 g of BOC-Tyr-(D)-Met-Gly-MePhe-NHNHCONH$_2$ followed by addition of 0.082 ml of 30% aqueous $H_2O_2$. The solution is stirred for 10 minutes, treated with 100 ml of ether and filtered to obtain a powder. Yield 0.35 g (88%); m.p. 110°–115° C.; $[\alpha]_D^{24} -35.1°$ (c=1.04, DMF); $Rf^1$ 0.05.

Elemental analysis, for $C_{32}H_{45}O_9N_7S.2H_2O$: Calcd. C, 51.95; H, 6.68; N, 13.25; S, 4.33. Found C, 52.08; H, 6.32; N, 13.03; S, 4.43.

(VII) Production of H-Tyr-(D)-Met(O)-Gly-MePhe-NHNHCONH$_2$

To 0.25 g of BOC-Tyr-(D)-Met(O)-Gly-MePhe-NHNHCONH$_2$ are added 0.2 ml of anisole and 4 ml of TFA, and the mixture is shaken for 10 minutes and concentrated. The residue is treated with ether and filtered to obtain a powder. This powder is dissolved in 10 ml of water and passed through a column (1×10 cm) of Amberlite IRA 410 (acetate-form) and, then, a column (2.2×120 cm) of Sephadex LH-20. Elution is carried out with 0.1 N acetic acid and the fractions from 290 to 325 ml are pooled and lyophilized. Yield 185 mg; $[\alpha]_D^{24} -19.9°$ (c=0.72, MeOH); $Rf^2$ 0.12.

Amino acid analysis (hydrolysis with 4% thioglycolic acid-6 N HCl): Gly 0.96(1); Met 0.95(1); Tyr 1.08(1); MePhe 1.00(1).

EXAMPLE 2

Production of H-Tyr-(D)-Ala-Gly-MePhe-NHNHCONH$_2$

(I) Production of Z-Tyr-(D)-Ala-Gly-OH

In 200 ml of MeOH is dissolved 8.2 g of Z-(D)-Ala-Gly-OBu$^t$ and catalytic reduction is carried out in the presence of palladium black catalyst. The catalyst is filtered off, the MeOH is distilled off and the residue is dissolved in 70 ml of trifluoroacetic acid and allowed to stand at room temperature for 40 minutes. The trifluoroacetic acid is distilled off and the residue is treated with ether and filtered. The powder thus obtained is suspended in 50 ml of water and 4.7 g of sodium hydrogen carbonate is added and dissolved. To this solution is added 100 ml of a THF solution containing 13.3 g (28 mM) of Z-Tyr-ONB and the mixture is stirred at room temperature overnight. The reaction mixture is neutralized with 1 N-HCl and extracted with 150 ml of AcOEt. The extract is washed with water and dried over anhydrous sodium sulfate. The AcOEt is distilled off and the residue is treated with ether, filtered and recrystallized from AcOEt.

Yield 8.5 g (69%), m.p. 184°–185° C.; $[\alpha]_D^{22} +25.6°$ (c=0.5, MeOH); $Rf^1$=0.16.

Elemental analysis, for $C_{22}H_{25}O_7N_3$: Calcd. C, 59.58; H, 5.68; N, 9.48. Found C, 59.29; H, 5.81; N, 9.32.

(II) Production of Z-Tyr-(D)-Ala-Gly-MePhe-NHNHCONH$_2$

One (1.0) gram of Z-MePhe-NHNHCONH$_2$ is subjected to catalytic reduction in methanol, the solvent is distilled off and the residue is dissolved in 20 ml of DMF. To this solution are added 1.2 g of Z-Tyr-(D)-Ala-Gly-OH and 0.41 g of HOBt and after cooling with ice, 0.69 g of DCC is added. The mixture is stirred for 24 hours. The DCU is filtered off, the solvent is distilled off and the residue is dissolved in n-butanol-containing ethyl acetate. The solution is washed with aqueous sodium hydrogen carbonate and aqueous sodium chloride and dried over anhydrous sodium sulfate. The solvent is distilled off and the residue is dissolved in chloroform and chromatographed on a silica gel column (3.8×7 cm), elution being carried out with chloroform-methanol-acetic acid (9:1:0.5). The fractions from 120 ml of 360 ml are pooled, concentrated and treated with ether to obtain a powder. Yield 0.84 g (45.2%); m.p. 108°–111° C.; $[\alpha]_D^{21.5} -27.7°$ (c=0.98 MeOH), $Rf^1$ 0.14.

Elemental analysis, for $C_{33}H_{39}O_8N_7.3H_2O$: Calcd. C, 57.55; H, 6.15; N, 14.24. Found C, 57.39; H, 5.72; N, 13.78.

(III) Production of H-Tyr-(D)-Ala-Gly-MePhe-NHNHCONH$_2$

In 50 ml of methanol is dissolved 0.41 g of Z-Tyr-(D)-Ala-Gly-MePhe-NHNHCONH$_2$ and catalytic reduction is carried out in the conventional manner. The catalyst is filtered off, the solvent is distilled off, and a small amount of acetic acid is added. The mixture is passed over a column (2.2×120 cm) of Sephadex LH-20, elution is carried out with 0.1 N acetic acid, and the fractions from 310 ml to 370 ml are pooled and lyophilized.

Yield 0.30 g; $[\alpha]_D^{24} -14.7°$ (c=0.55, methanol); $Rf^2$ 0.25.

Aminoacid analysis: Gly 0.96(1); Ala 1.00(1); Tyr 0.92(1); MePhe 1.13(1).

EXAMPLE 3

Production of H-Tyr-(D)-Met(O)-Gly-Phe-NHNHCONH$_2$

(I) Production of Z-Phe-NHNHCONH$_2$

In 5 ml of water is dissolved 2.50 g (22 mM) of NH$_2$NHCONH$_2$.HCl, the solution is neutralized with 3.14 ml of TEA, and 40 ml of DMF is added. To this solution are added 3.0 g of Z-Phe-OH, 2.0 g of HONB and 2.3 g of DCC. The mixture is stirred for 24 hours, the precipitated DCU filtered off, the solvent distilled off and the residue dissolved in 200 ml of ethyl acetate. The solution is washed with aqueous sodium hydrogen carbonate and water in that order and dried over anhydrous sodium sulfate. The solvent is then distilled off, the residue is treated with ether, and crystals are collected by filtration. Yield 2.7 g; m.p. 119°–121° C., $[\alpha]_D^{21.5} -14.4°$ (c=1.01, DMF), $Rf^1$ 0.29.

Elemental analysis, for $C_{18}H_{20}O_4N_4.\frac{1}{2}H_2O$: Calcd. C, 59.16; H, 5.79; N, 15.34. Found C, 59.36; H, 5.74; N, 15.74.

(II) Production of BOC-Tyr-(D)-Met-Gly-Phe-NHNHCONH$_2$

In 30 ml of methanol is dissolved 1.0 g of Z-Phe-NHNHCONH$_2$ and catalytic reduction is carried out in the presence of palladium black catalyst for 3 hours. The catalyst is filtered off, the filtrate concentrated and the residue dissolved in 20 ml of DMF. To this solution are added 1.24 g of BOC-Tyr-(D)-Met-Gly-OH and 0.50 g of HONB, and after cooling with ice, 0.58 g of DCC is added and stirred for 24 hours. The precipitated DCU is filtered off, the solvent is distilled off and the residue is dissolved in n-butanol, washed with aqueous sodium hydrogen carbonate and aqueous sodium chloride in the order mentioned and dried over anhydrous sodium sulfate. The solvent is distilled off and the residue is treated with ether and filtered to obtain crystals. These crystals are recrystallized from methanol-ether. Yield 1.50 g; m.p. 202°–203° C. (decompn.); $Rf^1$ 0.23; $[\alpha]_D^{21.5} +29.1°$ (c=1.09, MeOH).

Elemental analysis, for $C_{31}H_{43}O_8N_7S \cdot 4H_2O$: Calcd. C, 49.91; H, 6.89; N, 13.15; S, 4.30. Found C, 49.61; H, 6.98; N, 12.99; S, 3.92.

(III) Production of
BOC-Tyr-(D)-Met(O)-Gly-Phe-NHNHCONH$_2$

In 5 ml of acetic acid is dissolved 900 mg of BOC-Tyr-(D)-Met-Gly-Phe-NHNHCONH$_2$ followed by addition of 0.24 ml of 30% aqueous $H_2O_2$. The solution is stirred for 10 minutes, treated with 100 ml of ether and filtered to obtain a powder. Yield 760 mg; m.p. 114°–121° C.; $[\alpha]_D^{21.5} -2.6°$ (c=0.89, DMF); $Rf^2$ 0.38.

Elemental analysis, for $C_{31}H_{43}O_9N_7S \cdot 4H_2O$: Calcd. C, 48.87; H, 6.75; N, 12.87; S, 4.21. Found C, 48.74; H, 6.08; N, 12.92; S, 4.06.

(IV) Production of
H-Tyr-(D)-Met(O)-Gly-Phe-NHNHCONH$_2$

To 400 mg of BOC-Tyr-(D)-Met(O)-Gly-Phe-NHNHCONH$_2$ is added 0.2 ml of anisole followed by addition of 5 ml of trifluoroacetic acid. The mixture is stirred at room temperature for 10 minutes and concentrated. The residue is treated with ether and filtered to obtain a powder. This powder is dissolved in 10 ml of water and the solution is passed over Amberlite IRA 410 (acetate-form), an ion exchange resin, and, then, over a column (2.2×120 cm) of Sephadex LH-20, elution being carried out with 0.1 N acetic acid. The fractions from 285 ml to 335 ml are pooled and lyophilized. Yield 300 mg, $[\alpha]_D^{21.5} +24.9°$ (c=0.76, MeOH); $Rf^2$ 0.08.

Amino acid analysis (hydrolysis with 4% thioglycolic acid-6 N HCl): Gly 0.98(1); Met 1.00(1); Tyr 1.01(1); Phe 1.04(1).

EXAMPLE 4

Production of H-Tyr-(D)-Ala-Gly-Phe-NHNHCONH$_2$ (I) Production of
Z-Tyr-(D)-Ala-Gly-Phe-NHNHCONH$_2$ In 30 ml of methanol is dissolved 1.0 g of Z-Phe-NHNHCONH$_2$ and catalytic reduction is carried out in the presence of Pd black catalyst for 3 hours. The catalyst is filtered off, the filtrate concentrated and the residue dissolved in 20 ml of DMF. To this solution are added 1.11 g of Z-Tyr-(D)-Ala-GlyOH and 0.50 g of HONB, and after cooling with ice, 0.58 g of DCC is added and stirred for 24 hours. The precipitated DCU is filtered off, the solvent is distilled off and the residue is dissolved in n-butanol-ethyl acetate, washed with aqueous sodium hydrogen carbonate and aqueous sodium chloride and dried over anhydrous sodium sulfate. The solvent is distilled off and the residue is treated with ether and filtered to obtain a powder. Yield 1.50 g; m.p. 181°–185° C.; $Rf^1$ 0.15; $[\alpha]_D^{21.5} -22.6°$ (c=1.01, DMF).

Elemental analysis, for $C_{32}H_{37}O_8N_7 \cdot H_2O$: Calcd. C, 57.73; H, 5.91; N, 14.73. Found C, 57.77; H, 5.72; N, 14.66.

(II) Production of
H-Tyr-(D)-Ala-Gly-Phe-NHNHCONH$_2$

In 20 ml of acetic acid is dissolved 500 mg of Z-Tyr-(D)-Ala-Gly-Phe-NHNHCONH$_2$ and catalytic reduction is carried out in the presence of Pd black catalyst for 3 hours. The catalyst is filtered off and the solvent distilled off. The residue is dissolved in 5 ml of 0.1 N acetic acid and passed over a column (2.2×120 cm) of Sephadex LH-20. Elution is carried out with 0.1 N acetic acid and the fractions from 300 ml to 350 ml are pooled and lyophilized. Yield 330 mg; $[\alpha]_D^{21.5} +15.3°$ (c=0.58, MeOH); $Rf^2$ 0.18.

Amino acid analysis: Gly 1.00(1); Ala 1.00(1); Tyr 0.99(1); Phe 1.06(1).

EXAMPLE 5

Production of
H-Tyr-(D)-Met(O)-Gly-MePhe-NHNHCSNH$_2$ (I) Production of Z-MePhe-NHNHCSNH$_2$ In 30 ml of DMF are dissolved 3.13 g of Z-MePhe-OH and 1.10 g of NH$_2$NHCSNH$_2$, and after ice-cooling, 1.97 g of HONB and 2.27 g of DCC are added. The mixture is stirred for 48 hours. The precipitated DCU is filtered off, the solvent is distilled off and the residue is dissolved in 50 ml of ethyl acetate, washed with aqueous sodium hydrogen carbonate and 1 N-aqueous HCl and dried over anhydrous sodium sulfate. The solvent is distilled off and the residue is treated with petroleum benzin to obtain a powder. Yield 3.60 g; m.p. 83°–86° C.; $Rf^1$ 0.62; $[\alpha]_D^{21.5} -69.7°$ (c=0.95, DMF).

Elemental analysis, for $C_{19}H_{22}O_3N_4S$: Calcd. C, 59.04; H, 5.74; H, 14.50; S, 8.30. Found C, 59.07; H, 5.73; N, 14.49; S, 8.00.

(II) Production of BOC-Tyr-(D)-Met(O)-Gly-OH

In a mixture of 7 ml of acetic acid and 7 ml of EtOH is dissolved 3.0 g of BOC-Tyr-(D)-Met-Gly-OH, and 1.0 ml of 30% aqueous $H_2O_2$ is added dripwise at room temperature. The solution is stirred for 10 minutes, treated with 100 ml of ether and filtered to obtain a powder. Yield 2.50 g; m.p. 183°–184° C. (decompn.); $Rf^2$ 0.20; $[\alpha]_D^{21.5} +2.1°$ (c=0.89, DMF).

Elemental analysis, for $C_{21}H_{31}O_8N_3S \cdot H_2O$: Calcd. C, 50.08; H, 6.61; N, 8.35; S, 6.37. Found C, 50.58; H, 6.34; N, 8.47; S, 6.25.

(II) Production of
BOC-Tyr-(D)-Met(O)-Gly-MePhe-NHNHCSNH$_2$

To 0.5 g of Z-MePhe-NHNHCSNH$_2$ are added 0.35 ml of anisole and 8 ml of 25% HBr-acetic acid. The mixture is shaken at room temperature for 30 minutes, treated with ether and filtered to obtain a powder. The resulting powder is dried and dissolved in 10 ml of DMF. To this solution are added 0.67 g of BOC-Tyr-(D)-Met(O)-Gly-OH and 0.21 g of HOBT, and after ice-cooling, 0.32 g of DCC is added. The mixture is stirred for 24 hours, the precipitated DCU filtered off, the solvent distilled off and the residue dissolved in n-butanol-ethyl acetate. The solution is washed with aqueous sodium hydrogen carbonate and water in that order and dried over anhydrous sodium sulfate. The solvent is distilled off and the residue is dissolved in 20 ml of chloroform and chromatographed on a silica gel column (3.8×5.5 cm), elution being carried out with chloroform-MeOH-AcOH (9:1:0.5). The fractions from 155 to 345 ml are pooled, concentrated, treated with ether and filtered to obtain a powder. Yield 0.45 g; m.p. 167°–169° C. (decompn.); $Rf^1$ 0.14; $[\alpha]_D^{21.5}$ −26.7° (c=0.87, MeOH).

Elemental analysis, for $C_{32}H_{45}O_8N_7S_2 \cdot H_2O$: Calcd. C, 52.08; H, 6.42; N, 13.29; S, 8.69. Found C, 52.43; H, 6.28; N, 13.11; S, 8.35.

(IV) Production of H-Tyr-(D)-Met(O)-Gly-MePhe-NHNHCSNH₂

To 300 mg of BOC-Tyr-(D)-Met(O)-Gly-MePhe-NHNHCSNH₂ are added 0.2 ml of anisole and 5 ml of TFA, and the mixture is shaken at room temperature for 10 minutes. The solvent is then distilled off and the residue is treated with ether and filtered to obtain a powder. This powder is dissolved in 10 ml of water and the solution is passed through a column (1×10 cm) of Amberlite IRA-410 (acetate-form), an ion exchange resin, and, then, over a column (2.2×120 cm) of Sephadex LH-20, elution being carried out with 0.1 N acetic acid. The fractions from 330 to 390 ml are pooled and lyophilized. Yield 90 mg; $[\alpha]_D^{21.5}$ −41.1° (c=0.44, MeOH); $Rf^2$ 0.16.

Amino acid analysis (hydrolysis with 4% thioglycolic acid-6 N HCl): Gly 0.92(1); Met 0.98(1); Tyr 1.00(1); MePhe 1.16(1).

EXAMPLE 6

Production of H-Tyr-(D)-Ala-Gly-MePhe-NHNHCSNH₂

(I) Production of Z-Tyr-(D)-Ala-Gly-MePhe-NHNHCSNH₂

To 0.5 g of Z-MePhe-NHNHCSNH₂ are added 0.35 ml of anisole and 8 ml of 25% HBr-acetic acid, and the mixture is shaken at room temperature for 30 minutes, treated with ether and filtered to obtain a powder. This powder is dried and dissolved in 10 ml of DMF. To this solution are added 0.58 g of Z-Tyr-(D)-Ala-Gly-OH and 0.21 g of HOBT, and after ice-cooling, 0.32 g of DCC is added. The mixture is stirred for 24 hours, the precipitated DCU filtered off, the solvent distilled off and the residue dissolved in n-butanol-ethyl acetate. The solution is washed with aqueous sodium hydrogen carbonate and water in that order and dried over anhydrous sodium sulfate. The solvent is distilled off and the residue dissolved in 20 ml of chloroform and chromatographed on a silica gel column (3.8×5.5 cm), elution being carried out with chloroform-methanol-acetic acid (38:2:1). The fractions from 295 to 580 ml are pooled, treated with ether and filtered to obtain a powder. Yield 0.395 g; m.p. 135°–140° C.; $Rf^1$ 0.30; $[\alpha]_D^{21.5}$ −60.3° (c=0.90, DMF).

Elemental analysis, for $C_{33}H_{39}O_7N_7S \cdot \frac{1}{2}H_2O$: Calcd. C, 57.71; H, 5.87; N, 14.28; S, 4.67. Found C, 57.57; H, 5.76; N, 14.22; S, 3.56.

(II) Production of H-Tyr-(D)-Ala-Gly-MePhe-NHNHCSNH₂

To 40 mg of Z-Tyr-(D)-Ala-Gly-MePhe-NHNHCSNH₂ are added 0.1 ml of anisole and 0.5 ml of 25% HBr/AcOH and the mixture is shaken at room temperature for 60 minutes, treated with ether and filtered to obtain a powder. This powder is dissolved in 5 ml of water and the solution is passed through Amberlite IRA-410 (acetate-form), an ion exchange resin, and, then, over a column (2.2×120 cm) of Sephadex LH-20, elution being carried out with 0.1 N acetic acid. The fractions from 365 to 410 ml are pooled and lyophilized. Yield 13 mg; $[\alpha]_D^{24}$ −39.0° (c=0.4, MeOH); $Rf^2$ 0.33.

Amino acid analysis: Ala 1.05(1); Gly 1.00(1); Tyr 0.92(1); MePhe 1.03(1).

EXAMPLE 7

Production of H-Tyr-(D)-Gln-Gly-MePhe-NHNHCONH₂

(I) Production of Z-Gly-MePhe-NHNHCONH₂

In 30 ml of methanol is dissolved 1.5 g of Z-MePhe-NHNHCONH₂ and catalytic reduction is carried out in the presence of Pd black catalyst. The catalyst is filtered off, the filtrate concentrated and the residue dissolved in 20 ml of DMF. To this solution are added 0.85 g of Z-Gly-OH and 0.80 g of HONB, and after ice-cooling, 0.92 g of DCC is added and stirred for 15 hours. The precipitated DCU is filtered off, the solvent is distilled off and the residue is dissolved in 50 ml of ethyl acetate, washed with 1 N-HCl and aqueous sodium hydrogen carbonate and dried over anhydrous sodium sulfate. The solvent is distilled off and the residue is dissolved in 10 ml of chloroform and subjected to silica gel column (3.5×5.5 cm) chromatography, elution being carried out with 5% MeOH. The fraction from 240 ml of 770 ml are pooled, concentrated, treated with ether and filtered to obtain a powder. Yield 0.76 g; m.p. 83°–86° C.: $[\alpha]_D^{24}$ −56.8° (c=0.9, DMF); $Rf^1$ 0.39.

Elemental analysis, for $C_{21}H_{25}O_5N_5$: Calcd. C, 59.00; H, 5.90; N, 16.39. Found C, 58.87; H, 6.10; N, 16.20.

(II) Production of BOC-(D)-Gln-Gly-MePhe-NHNHCONH₂

0.85 g of Z-Gly-MePhe-NHNHCONH₂ is subjected to catalytic reduction in methanol, dissolved in 10 ml of DMF, and after ice-cooling, 0.50 g of BOC-(D)-Gln-OH, 0.40 g of HONB and 0.45 g of DCC are added. The mixture is stirred for 15 hours, the precipitated DCU filtered off and the solvent distilled off. The residue is dissolved in n-butanol, washed with a saturated aqueous solution of sodium hydrogen carbonate and water in that order and dried over anhydrous sodium sulfate. The solvent is distilled off, treated with ether and filtered to obtain a powder. Yield 0.82 g; m.p. 124°–128° C.; $[\alpha]_D^{24}$ −36.5° (c=1.0, DMF); $Rf^1$ 0.11.

Elemental analysis, for $C_{23}H_{35}O_7N_7$: Calcd. C, 52.96; H, 6.76; N, 18.80. Found C, 52.65; H, 6.62; N, 18.61.

(III) Production of Z-Tyr-(D)-Gln-Gly-MePhe-NHNHCONH₂

In 10 ml of trifluoroacetic acid is dissolved 0.70 g of BOC-(D)-Gln-Gly-MePhe-NHNHCONH₂, and the solution is shaken for 10 minutes and concentrated. The residue is treated with ether and filtered to obtain a powder. This powder is dissolved in 10 ml of DMF and the solution is neutralized with 0.20 ml of TEA, and 0.64 g of Z-TyrONB is added. The mixture is stirred for 15 hours. The DMF is distilled off, treated with ethyl acetate and filtered to obtain a powder, which is further reprecipitated from methanol-ether. Yield 0.73 g; m.p. 135°–139° C.; $[\alpha]_D^{24}$ −53.1° (c=0.9, DMF); $Rf^1$ 0.08.

Elemental analysis, for $C_{35}H_{42}O_9N_8$: Calcd. C, 58.48; H, 5.89; N, 15.59. Found C, 58.05; H, 6.02; N, 15.23.

(IV) Production of H-Tyr-(D)-Gln-Gly-MePhe-NHNHCONH$_2$

In a mixture of 50 ml of methanol and 5 ml of acetic acid is dissolved 0.50 g of Z-Tyr-(D)-Gln-Gly-MePhe-NHNHCONH$_2$ and catalytic reduction is carried out for 5 hours. The catalyst is filtered off, the solvent is distilled off and the residue is dissolved in a small amount of 0.1 N acetic acid. The solution is chromatographed on a column (2.2×120 cm) of Sephadex LH-20 and elution is carried out with 0.1 N acetic acid. The fractions from 300 to 345 ml are pooled and lyophilized. Yield 350 mg; $[\alpha]_D^{24}-20.1°$ (c=0.4, MeOH); Rf$^2$ 0.14.

Amino acid analysis: Glu 1.05(1); Gly 1.00(1); Tyr 0.93(1); MePhe 0.97(1).

EXAMPLE 8

Production of H-Tyr-(D)-Asn-Gly-MePhe-NHNHCONH$_2$

(I) Production of BOC-(D)-Asn-Gly-MePhe-NHNHCONH$_2$ 0.85 g of Z-Gly-MePhe-NHNHCONH$_2$ is subjected to catalytic reduction in methanol, dissolved in 10 ml of DMF, and after ice-cooling, 0.46 g of BOC-(D)-Asn-OH, 0.40 g of HONB and 0.45 g of DCC are added. The mixture is stirred for 15 hours. The precipitated DCU is filtered off, the solvent is distilled off and the residue is dissolved in n-butanol. The solution is washed with saturated aqueous sodium hydrogen carbonate and aqueous sodium chloride in that order and dried over anhydrous sodium sulfate. The solvent is distilled off, ether is added to the residue and the mixture is filtered to obtain a powder. Yield 0.78 g; m.p. 133°–136° C.; $[\alpha]_D^{24}-36.5°$ (c=1.0, DMF); Rf$^1$ 0.09.

Elemental analysis, for $C_{22}H_{33}O_7N_7$: Calcd. C, 52.06; H, 6.55; N, 19.32. Found C, 51.74; H, 6.66; N, 19.03.

(II) Production of Z-Tyr-(D)-Asn-Gly-MePhe-NHNHCONH$_2$

In 10 ml of trifluoroacetic acid is dissolved 0.78 g of BOC-(D)-Asn-Gly-MePhe-NHNHCONH$_2$, and the solution is shaken for 10 minutes and concentrated. The residue is treated with ether and filtered to obtain a powder. This powder is dissolved in 10 ml of DMF, the solution is neutralized with 0.20 ml of TEA, and 0.64 g of Z-Tyr-ONB is added. The mixture is stirred for 24 hours. The DMF is distilled off and the residue is treated with ethyl acetate and filtered to obtain a powder, which is further reprecipitated from methanol-ether. Yield 0.65 g; m.p. 141°–144° C.; $[\alpha]_D^{24}-50.5°$ (c=1.1, DMF); Rf$^1$ 0.07.

Elemental analysis, for $C_{34}H_{40}O_9N_8 \cdot H_2O$: Calcd. C, 56.50; H, 5.86; N, 15.51. Found C, 56.23; H, 5.77; N, 15.34.

(III) Production of H-Tyr-(D)-Asn-Gly-MePhe-NHNHCONH$_2$

In a mixture of 40 ml of methanol and 3 ml of acetic acid is dissolved 0.40 g of Z-Tyr-(D)-Asn-Gly-MePhe-NHNHCONH$_2$ and catalytic reduction is carried out for 7 hours. The catalyst is filtered off, the solvent is distilled off and the residue is dissolved in a small amount of 0.1 N acetic acid. The solution is chromatographed on a column (2.2×120 cm) of Sephadex LH-20 and elution is carried out with 0.1 N acetic acid. The fractions from 295 to 330 ml are pooled and lyophilized. Yield 270 mg; $[\alpha]_D^{24}-18.6°$ (c=0.3, MeOH); Rf$^2$ 0.13.

Amino acid analysis: Asn 0.98(1); Gly 1.00(1); Tyr 0.92(1); MePhe 0.98(1).

EXAMPLE 9

Production of H-Tyr-(D)-Gln-Gly-MePhe-NHNHCSNH$_2$

(I) Production of BOC-Gly-MePhe-NHNHCSNH$_2$

To 3.5 g of Z-MePhe-NHNHCSNH$_2$ are added 1 ml of anisole and 30 ml of 25% HBr-acetic acid. The mixture is shaken at room temperature for 60 minutes, treated with ether and filtered to obtain a powder. This powder is dried and dissolved in 50 ml of DMF, and after ice-cooling, the solution is neutralized with 2.5 ml of TEA followed by addition of 1.60 g of BOC-Gly-OH, 1.40 g of HOBT and 2.10 g of DCC. The mixture is stirred for 24 hours. The solvent is distilled off and the residue is treated with ethyl acetate, washed with 10% citric acid, aqueous sodium hydrogen carbonate and water in that order and dried over anhydrous sodium sulfate. The solvent is distilled off and the residue is dissolved in chloroform and chromatographed on a silica gel column (5.5×10 cm), elution being carried out with 2% methanol-chloroform. The fractions from 1.6 l to 3.2 l are pooled, concentrated and treated with ether to obtain a powder. Yield 2.1 g; m.p. 85°–90° C.; $[\alpha]_D^{24}-82.8°$ (c=1.1, DMF), Rf$^1$ 0.63.

Elemental analysis, for $C_{21}H_{25}O_4N_5S$: Calcd. C, 56.87; H, 5.68; N, 15.79; S, 7.23. Found C, 56.78; H, 5.60; N, 15.48; S, 7.01.

(II) Production of BOC-(D)-Gln-Gly-MePhe-NHNHCSNH$_2$

In 10 ml of trifluoroacetic acid is dissolved 0.80 g of BOC-Gly-MePhe-NHNHCSNH$_2$, and the solution is shaken for 10 minutes, concentrated, treated with ether and filtered to obtain a powder. This powder is dissolved in 10 ml of DMF, and after ice-cooling, the solution is neutralized with 10 ml of DMF and 0.05 g BOC-(D)-Gln-OH, 0.40 g of HONB and 0.45 g of DCC are added. The mixture is stirred for 20 hours. The precipitated DCU is filtered off, the solvent distilled off and the residue dissolved in n-butanol. The solution is washed with a saturated aqueous solution of sodium hydrogen carbonate and water in that order and dried over anhydrous sodium sulfate. The solvent is distilled off and the residue is treated with ether and filtered to obtain a powder. Yield 0.73 g; m.p. 120°–123° C.; $[\alpha]_D^{24}-46.0°$ (c=1.0, DMF); Rf$^1$ 0.18.

Elemental analysis, for $C_{23}H_{25}O_6N_7S$: Calcd. C, 51.38; H, 4.69; N, 18.24; S, 5.96. Found C, 50.95; H, 4.33; N, 18.03; S, 5.76.

(III) Production of Z-Tyr-(D)-Gln-Gly-MePhe-NHNHCSNH$_2$ 0.60 g of BOC-(D)-Gln-Gly-MePhe-NHNHCSNH$_2$ is treated with trifluoroacetic acid and dissolved in 10 ml of DMF. The solution is neutralized with 0.19 ml of TEA, and 0.54 g of Z-Tyr ONB is added. The mixture is stirred for 15 hours. The DMF is distilled off and the residue is treated with ethyl acetate and filtered to obtain a powder, which is further reprecipitated from methanol-ether. Yield 0.54 g; m.p. 128°–133° C.; $[\alpha]_D^{24}-72.4°$ (c=1.1, DMF); Rf$^1$ 0.13.

Elemental analysis, for $C_{35}H_{42}O_8N_8S$: Calcd. C, 57.20; H, 5.76; N, 15.25; S, 4.36. Found C, 56.85; H, 5.53; N, 15.41; S, 4.07.

(IV) Production of H-Tyr-(D)-Gln-Gly-MePhe-NHNHCSNH$_2$

To 0.40 g of Z-Tyr-(D)-Gln-Gly-MePhe-NHNHCSNH$_2$ are added 0.2 ml of anisole and 4 ml of 25% HBr-acetic acid and the mixture is shaken at room temperature for 60 minutes, treated with ether and filtered to obtain a powder. This powder is dried and dissolved in a small amount of water. The solution is passed through a column (1×10 cm) of Amberlite IRA 410 (acetate-form), an ion exchange resin, and lyophilized. The lyophilizate is dissolved in a small amount of 0.1 N acetic acid and passed over a column (2.2×120 cm) of Sephadex LH-20. Elution is carried out with 0.1 N acetic acid and the fractions from 350 to 395 ml are pooled and lyophilized. Yield 110 mg; $[\alpha]_D^{24}-43.2°$ (c=0.3, MeOH); $Rf^2$ 0.19.

Amino acid analysis: Glu 0.95(1); Gly 1.00(1); Tyr 0.97(1); MePhe 1.05(1).

EXAMPLE 10

Production of H-Tyr-(D)-Asn-Gly-MePhe-NHNHCSNH$_2$

(I) Production of BOC-(D)-Asn-Gly-MePhe-NHNHCSNH$_2$

In 10 ml of trifluoroacetic acid is dissolved 0.80 g of BOC-Gly-MePhe-NHNHCSNH$_2$ and the solution is shaken for 10 minutes, concentrated, treated with ether and filtered to obtain a powder. This powder is dissolved in 10 ml of DMF, and after ice-cooling, the solution is neutralized with 0.20 ml of TEA followed by addition of 0.47 g of BOC-(D)-Asn-OH, 0.40 g of HONB and 0.45 g of DCC. The mixture is stirred for 20 hours, the precipitated DCU filtered off, the solvent distilled off and the residue dissolved in n-butanol. The solution is washed with a saturated aqueous solution of sodium hydrogen carbonate and water in that order and dried over anhydrous sodium sulfate. The solvent is distilled off and the residue is treated with ether and filtered to obtain a powder, which is further reprecipitated from methanol-ether. Yield 0.69 g; m.p. 124°–127° C.; $[\alpha]_D^{24}-42.5°$ (c=1.0, DMF); $Rf^1$ 0.16.

Elemental analysis, for $C_{22}H_{33}O_6N_7S$: Calcd. C, 50.46; H, 6.35; N, 18.73; S, 6.12. Found C, 50.05; H, 6.32; N, 18.56; S, 5.88.

(II) Production of Z-Tyr-(D)-Asn-Gly-MePhe-NHNHCSCH$_2$ 0.58 g of BOC-(D)-Asn-Gly-MePhe-NHNHCSNH$_2$ is treated with trifluoroacetic acid, dissolved in 10 ml of DMF, neutralized with 0.19 ml of TEA, and 0.54 g of Z-Tyr-ONB is added. The mixture is stirred for 20 hours. The DMF is distilled off and the residue treated with ethyl acetate and filtered to obtain a powder, which is further reprecipitated from methanol-ether. Yield 0.50 g; m.p. 134°–137° C.; $[\alpha]_D^{24}-68.2°$ (c=1.0 in DMF); $Rf^1$ 0.12.

Elemental analysis, for $C_{34}H_{40}O_8N_8S$: Calcd. C, 56.65; H, 5.59; N, 15.55; S, 4.45. Found C, 56.17; H, 5.30; N, 15.60; S, 4.21.

(III) Production of H-Tyr-(D)-Asn-Gly-MePhe-NHNHCSNH$_2$

To 0.30 g of Z-Tyr-(D)-Asn-Gly-MePhe-NHNHCSNH$_2$ are added 0.15 ml of anisole and 3 ml of 25% HBr-acetic acid and the mixture is shaken at room temperature for 60 minutes, treated with ether and filtered to obtain a powder. This powder is dried and dissolved in a small of water. The solution is passed through a column (1×10 cm) of Amberlite IRA 410 (acetate-form), an ion exchange resin, and lyophilized. The lyophilizate is dissolved in a small amount of acetic acid and passed over a column (2.2×120 cm) of Sephadex LH-20. Elution is carried out with 0.1 N acetic acid and the fractions from 345 to 380 ml are pooled and lyophilized. Yield 95 mg; $[\alpha]_D^{24}-38.6°$ (c=0.4, MeOH); $Rf^2$ 0.17.

Amino acid analysis: Asp 1.05(1); Gly 1.00(1); Tyr 0.96(1); MePhe 1.08(1).

EXAMPLE 11

Production of H-Tyr-(D)-Met(O)-Gly-EtPhe-NHNHCONH$_2$

(I) Production of BOC-(D)-Met-Gly-OEt

In 100 ml of THF are dissolved 10.0 g of BOC-(D)-Met-OH and 7.9 g of HONB, followed by cooling at 0° C. and adding 9.0 g of DCC, and the mixture is stirred at 0° C. for 6 hours. Insoluble matters are filtered out, and 5.9 g of H-Gly-OEt.HCl salt and 5.6 ml of TEA are added to the filtrate, which is then stirred overnight at room temperature. The THF is distilled off and the residue is extracted with 100 ml of AcOEt, followed by washing with water and drying over anhydrous sodium sulfate. The AcOEt is distilled off and the residue is crystallized with petroleum ether. Recrystallization from AcOEt-petroleum ether yields 9.8 g of the desired product, m.p. 55°–56° C., $Rf^1=0.70$, $[\alpha]_D^{21}+12.5°$ (c=0.67, DMF).

Elemental analysis, for $C_{14}H_{26}O_5N_2S$: Calcd. C, 50.28; H, 7.83; N, 8.37; S, 9.59. Found C, 50.88; H, 7.99; N, 8.46; S, 9.42.

(II) Production of BOC-Tyr-(D)-Met-Gly-OEt

In 15 ml of TFA is dissolved 3.0 g of BOC-(D)-Met-Gly-OEt, and the mixture is allowed to stand at room temperature for 10 minutes. The TFA is distilled off and the residue is treated with diethyl ether, followed by recovering by filtration. The resultant powder is dissolved in 20 ml of THF. After cooling, 1.6 ml of TEA and 4.0 g of BOC-Tyr-ONB are added, and the mixture is stirred overnight at room temperature. The THF is distilled off, and the residue is extracted with 100 ml of AcOEt, followed by washing with water and drying over anhydrous sodium sulfate. The AcOEt is distilled off and the residue is crystallized with petroleum ether. Recrystallization from AcOEt yields 3.1 g of the desired product, m.p. 121°–122° C., $Rf^1=0.62$, $[\alpha]_D^{21}+16.8°$ (c=0.40, DMF).

Elemental analysis, for $C_{23}H_{35}O_7N_3S$: Calcd. C, 55.51; H, 7.09; N, 8.44; S, 6.44. Found C, 55.32; H, 6.93; N, 8.25; S, 6.27.

(III) Production of BOC-Tyr-(D)-Met-Gly-OH

In 30 ml of MeOH is dissolved 2.8 g of BOC-Tyr-(D)-Met-Gly-OEt. After cooling, 12 ml of N-aqueous sodium hydroxide solution is added, and the mixture is stirred at room temperature for 1 hour. After cooling, 60 ml of 0.2 N-aqueous hydrochloric acid solution is added, and the precipitated crystals are collected by filtration, followed by washing with cold water. Thus obtained is 2.3 g of the desired product, m.p. 184°–186° C., $Rf^1 = 0.24$, $[\alpha]_D^{21} + 13.3°$ (c=0.46, DMF).

(IV) Production of Z-EtPhe-OH

In 150 ml of THF is dissolved 15 g of Z-PheOH. To the solution is added 32 ml of ethyl iodide. The mixture is cooled with ice, to which is added 6.6 g of oilness-sodium hydride, and the mixture is stirred for 7 days. To the reaction mixture is added 300 ml of ethyl acetate, and the mixture is stirred for two hours. To the mixture is added water, then, the solvent is distilled off. The solution is acidified with 1 N-HCl, and extracted with ethylacetate. The extract is washed with water and dried over anhydrous sodium sulfate. The solvent is distilled off and the residue is subjected to a silica gel column (6×14 cm) chromatography, elution being carried out with 2% MeOH-chloroform. The fractions from 700 ml to 1000 ml are pooled, concentrated. Yield 5.9 g (oil); $Rf^1$ 0.85.

(V) Production of Z-EtPhe-NHNHCONH$_2$

In 2 ml of water is dissolved 0.80 g of semicarbazide hydrochloride, and the solution is neutralized with 1.0 ml of TEA. To this solution 20 ml of DMF is added, followed by adding 2.1 g of Z-EtPhe-OH and 1.25 g of HONB. The mixture is cooled with ice, to which is added 1.60 g of DCC, followed by stirring overnight. The precipitated DCU is filtered off, the solvent is distilled off and the residue is dissolved in ethyl acetate. The solution is washed with aqueous sodium hydrogen carbonate and water in that order and dried over anhydrous sodium sulfate. The solvent is then distilled off, the residue is subjected to a silica gel column (3.6×7 cm) chromatography, elution being carried out with 5% MeOH-chloroform. The fractions from 170 ml to 340 ml are pooled, concentrated. The residue is treated with ether and filtered to obtain a powdery product. Yield 1.02 g; m.p. 55°–60° C.; $[\alpha]_D^{19} - 66.8°$ (c=1.06, DMF); $Rf^1$ 0.52.

Elemental analysis, for $C_{20}H_{24}O_4N_4$: Calcd. C, 62.48; H, 6.29; N, 14.58. Found C, 62.17; H, 6.08; N, 14.43.

(IV) Production of Boc-Tyr-(D)-Met-Gly-EtPhe-NHNHCONH$_2$

In 50 ml of methanol is dissolved 1.0 g of Z-Phe-NHNHCONH$_2$ and catalytic reduction is carried out in the presence of palladium black catalyst for 3 hours. The catalyst is filtered off, the filtrate concentrated and the residue dissolved in 30 ml of DMF. To this solution are added 0.99 g of BOC-Tyr-(D)-Met-Gly-OH and 1.0 g of HOBt, and after cooling with ice, 1.5 g of DCC is added and stirred overnight. The precipitated DCU is filtered off, the solvent is distilled off and the residue is dissolved in ethyl acetate, washed with 10% aqueous citric acid and 1 N -aqueous ammonia in the order mentioned and concentrated. The residue is subjected to a silica gel column (3.6×8 cm) chromatography, elution being carried out with 5% methanol-chloroform. The fractions 220 ml to 420 ml are pooled, concentrated. The residue is treated with ether and filtered to obtain a powder. Yield 0.30 g; m.p. 123°–125° C.; $[\alpha]_D^{19} - 6.2°$ (c=0.45, DMF); $Rf^1$ 0.29.

Elemental analysis, for $C_{33}H_{47}O_8N_7S \cdot 2H_2O$: Calcd. C, 53.71; H, 6.97; N, 13.29; S, 4.35. Found C, 53.79; H, 6.71; N, 12.81; S, 4.35.

(VII) Production of Boc-Tyr-(D)-Met(O)-Gly-EtPhe-NHNHCONH$_2$

In 2 ml of acetic acid is dissolved 0.26 g of Boc-Tyr-(D)-Met-Gly-EtPhe-NHNHCONH$_2$. After cooling, to the solution 0.08 ml of 30% hydrogen peroxide solution is added, and the mixture is stirred for 10 minutes. The reaction solution is treated with diethyl ether, followed by collecting by filtration. Yield 0.22 g; m.p. 142°–146° C., $[\alpha]_D^{19} - 11.8°$ (c=0.88, DMF), $Rf^1$ 0.07.

Elemental analysis, for $C_{33}H_{47}O_9N_7S \cdot 3H_2O$: Calcd. C, 51.35; H, 6.92; N, 12.70; S, 4.15. Found C, 51.93; H, 6.63; N, 12.47; S, 4.29.

(VIII) Production of H-Tyr-(D)-Met(O)-Gly-EtPhe-NHNHCONH$_2$

To 0.15 g of Boc-Tyr-(D)-Met(O)-Gly-EtPhe-NHNHCONH$_2$ is added 0.2 ml of anisole followed by addition of 4 ml of trifluoroacetic acid. The mixture is stirred at room temperature for 10 minutes and the solvent is distilled off. The residue is treated with ether and filtered to obtain a powder. This powder is dissolved in 10 ml of water and the solution is passed over Amberlite IRA 410 (acetate form), an ion exchange resin, and, then, over a column (2.2×120 cm) of Sephadex LH-20, elution being carried out with 0.1 N acetic acid. The fractions from 285 ml-340 ml are pooled and lyophilized. Yield 95 mg; $[\alpha]_D^{19} + 8.9$ (c=0.37, methanol); $Rf^2$ 0.11.

Amino acid analysis (hydolysis with thioglycolic acid-6 N HCl): Gly 0.97(1); Met 1.00(1); Tyr 1.05(1).

EXAMPLE 12

In 1 l of physiological saline is dissolved 3.0 g of the H-Tyr-(D)-Met(O)-Gly-MePhe-NHNHCONH$_2$ obtained in Example 1 and the solution is filtered through a microfilter and distributed into ampoules at the rate of 2.2 ml per ampoule. After sealing, the ampoules are sterilized at −10° C. for 30 minutes. The above procedure gives ampoules of H-Tyr-(D)-Met(O)-Gly-MePhe-NHNHCONH$_2$ for subcutaneous, intravenous or intramuscular administration.

EXAMPLE 13

In 1 l of distilled water is dissolved 1.0 g of the H-Tyr-(D)-Ala-Gly-MePhe-NHNH-CO-NH$_2$ obtained in Example 2 and, then, 10 g of mannitol is added and dissolved. The solution is sterilized through a microfilter and distributed into ampoules at the rate of 2 ml per ampoule. The Ampoules are dried in a freeze-dryer and sealed. The above procedure provides ampoules for extemporaneous administration. To use the ampoule, it is unsealed and dissolved for example in 2 ml of physiological saline to give an injectable solution for subcutaneous, intravenous or intramuscular administration.

What we claim is:

1. A compound of the formula:

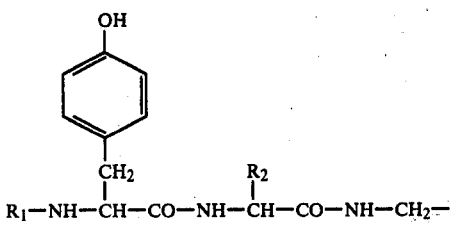
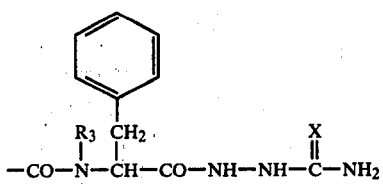

wherein $R_1$ is hydrogen or lower alkyl; $R_2$ is hydrogen or a side chain of a D-α-amino acid selected from the group consisting of D-leucine, D-alanine, D-methionine, D-methioninesulfoxide, D-methionine sulfone, D-serine, D-threonine, D-phenylalanine, D-α-aminobutyric acid, D-valine, D-norvaline, D-norleucine, D-isoleucine, D-histidine, D-tryptophan, D-tyrosine, D-glutamine, D-asparagine, D-arginine, D-lysine, D-ornithine, D-glutamic acid, D-aspartic acid, D-cysteine, S-methyl-D-cysteine, S-ethyl-D-cysteine, S-methyl-D-cysteine sulfoxide, S-ethyl-D-cysteine sulfoxide, S-methyl-D-methionine, O-t-butyl-D-serine, O-t-butyl-D-threonine, D-aspartic acid-β-methyl ester, and D-glutamic acid-γ-methyl ester; $R_3$ is hydrogen or lower alkyl; X is oxygen or sulfur, or a pharmacologically acceptable salt thereof.

2. The compound as claimed in claim 1, wherein $R_2$ is the side chain of D-α-amino acid selected from the group consisting of D-leucine, D-alanine, D-methionine, D-methioninesulfoxide, D-methionine sulfone, D-serine, D-threonine, D-phenylalanine, D-α-aminobutyric acid, D-valine, D-norvaline, D-norleucine, D-isoleucine, D-histidine, D-tryptophan, D-tyrosine, D-glutamine, D-asparagine, D-arginine, D-lysine, D-ornithine, D-glutamic acid, D-aspartic acid, D-cysteine, S-methyl-D-cysteine, S-ethyl-D-cysteine, S-methyl-D-cysteine sulfoxide, S-ethyl-D-cysteine sulfoxide, S-methyl-D-methionine, O-t-butyl-D-serine, O-t-butyl-D-threonine, D-aspartic acid-β-methyl ester, and D-glutamic acid-γ-methyl ester.

3. The compound as claimed in claim 1 wherein $R_1$ is hydrogen, $R_2$ is the side chain of D-α-methionine sulfoxide, $R_3$ is methyl and X is oxygen.

4. The compound as claimed in claim 1, wherein $R_1$ is hydrogen.

5. The compound as claimed in claim 1, wherein $R_2$ is the side chain of D-α-methioninesulfoxide.

6. The compound as claimed in claim 1, wherein $R_2$ is the side chain of D-α-alanine.

7. The compound as claimed in claim 1, wherein $R_2$ is the side chain of D-α-glutamine.

8. The compound as claimed in claim 1, wherein $R_2$ is the side chain of D-α-asparagine.

9. The compound as claimed in claim 1, wherein $R_3$ is hydrogen.

10. The compound as claimed in claim 1, wherein $R_3$ is alkyl having 1 to 3 carbon atoms.

11. The compound as claimed in claim 10, wherein $R_3$ is methyl.

12. The compound as claimed in claim 10, wherein $R_3$ is ethyl.

13. The compound as claimed in claim 1, wherein X is oxygen.

14. The compound as claimed in claim 1, wherein $R_1$ is hydrogen, $R_2$ is the side chain of D-α-methioninesulfoxide, $R_3$ is methyl and X is oxygen.

15. The compound as claimed in claim 1, wherein $R_1$ is hydrogen, $R_2$ is the side chain of D-α-alanine, $R_3$ is methyl and X is oxygen.

16. The compound as claimed in claim 1, wherein $R_1$ is hydrogen, $R_2$ is the side chain of D-α-methioninesulfoxide, $R_3$ is hydrogen and X is oxygen.

17. The compound as claimed in claim 1, wherein $R_1$ is hydrogen, $R_2$ is the side chain of D-α-alanine, $R_3$ is hydrogen and X is oxygen.

18. The compound as claimed in claim 1, wherein $R_1$ is hydrogen, $R_2$ is the side chain of D-α-methioninesulfoxide, $R_3$ is methyl and X is sulfur.

19. The compound as claimed in claim 1, wherein $R_1$ is hydrogen, $R_2$ is the side chain of D-α-alanine, $R_3$ is methyl and X is sulfur.

20. The compound as claimed in claim 1, wherein $R_1$ is hydrogen, $R_2$ is the side chain of D-α-glutamine, $R_3$ is methyl and X is oxygen.

21. The compound as claimed in claim 1, wherein $R_1$ is hydrogen, $R_2$ is the side chain of D-α-asparagine, $R_3$ is methyl and X is oxygen.

22. The compound as claimed in claim 1, wherein $R_1$ is hydrogen, $R_2$ is the side chain of D-α-glutamine, $R_3$ is methyl and X is sulfur.

23. The compound as claimed in claim 1, wherein $R_1$ is hydrogen, $R_2$ is the side chain of D-α-asparagine, $R_3$ is methyl and X is sulfur.

24. A method of producing a compound of the formula:

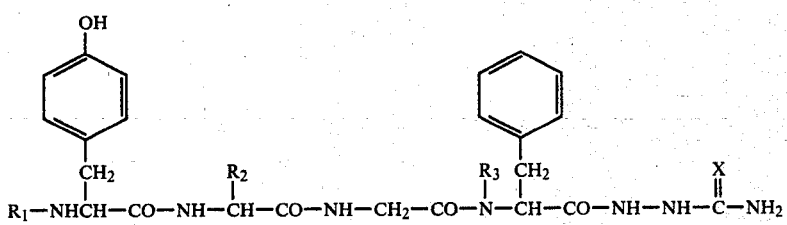

wherein $R_1$ is hydrogen or lower alkyl; $R_3$ is hydrogen or lower alkyl and X is oxygen or sulfur; $R_2$ is hydrogen or a D-α-amino acid side chain, or a pharmacologically acceptable salt thereof, which is characterized by deprotecting a compound of the formula:

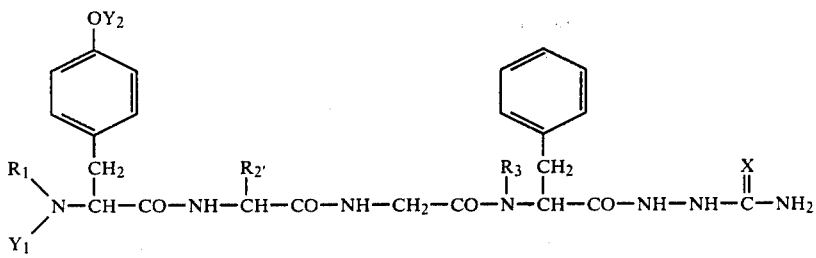

wherein $R_1$, $R_3$ and X are as defined above; $R_2'$ is hydrogen or a D-α-amino acid side chain which may optionally be protected; $Y_1$ is a protective group; $Y_2$ is hydrogen or a protective group.

25. A pharmaceutical composition for pain relieving in mammalian animals which contains an effective amount of a compound of the formula:

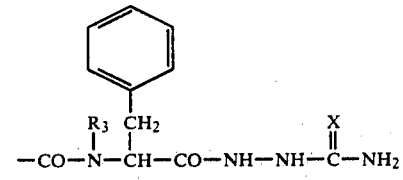

-continued

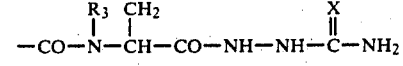

wherein $R_1$ is hydrogen or lower alkyl; $R_2$ is hydrogen or a side chain of a D-α-amino acid selected from the group consisting of D-leucine, D-alanine, D-methionine, D-methioninesulfoxide, D-methionine sulfone, D-serine, D-threonine, D-phenylalanine, D-α-aminobutyric acid, D-valine, D-norvaline, D-norleucine, D-isoleucine, D-histidine, D-tryptophan, D-tyrosine, D-glutamine, D-asparagine, D-arginine, D-lysine, D-ornithine, D-glutamic acid, D-aspartic acid, D-cysteine, S-methyl-D-cysteine, S-ethyl-D-cysteine, S-methyl-D-cysteine sulfoxide, S-ethyl-D-cysteine sulfoxide, S-methyl-D-methionine, O-t-butyl-D-serine, O-t-butyl-D-threonine, D-aspartic acid-β-methyl ester and D-glutamic acid-γ-methyl ester; $R_3$ is hydrogen or lower alkyl; X is oxygen or sulfur, and a pharmacologically acceptable carrier.

* * * * *